(12) United States Patent
Dennis et al.

(10) Patent No.: US 8,137,259 B1
(45) Date of Patent: **\*Mar. 20, 2012**

(54) MAGNETIC METHOD FOR TREATMENT OF AN ANIMAL

(75) Inventors: Robert Glenn Dennis, Chapel Hill, NC (US); Paul Edward Kosnik, Jonestown, TX (US); James Ronald Clark, Kingwood, TX (US)

(73) Assignee: Magnafix, LLC, Kingwood, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/952,797

(22) Filed: Nov. 23, 2010

Related U.S. Application Data

(60) Provisional application No. 61/265,716, filed on Dec. 1, 2009, provisional application No. 61/265,720, filed on Dec. 1, 2009.

(51) Int. Cl.
*A61N 1/00* (2006.01)
(52) U.S. Cl. ............................................. 600/14; 600/13
(58) Field of Classification Search .................. 600/9–15
See application file for complete search history.

(56) References Cited

U.S. PATENT DOCUMENTS

| | | | |
|---|---|---|---|
| 5,034,875 A | 7/1991 | Hattori | |
| 5,426,925 A | 6/1995 | Smargiassi | |
| 6,524,233 B2 | 2/2003 | Markoll | |
| 6,839,595 B2 | 1/2005 | Tepper et al. | |
| 7,175,587 B2 | 2/2007 | Gordon et al. | |
| 7,541,813 B2 | 6/2009 | Synder, Jr. et al. | |
| 2004/0172108 A1 | 9/2004 | Cochenour et al. | |
| 2005/0182287 A1 | 8/2005 | Becker | |
| 2008/0127899 A1 | 6/2008 | Angus | |
| 2009/0216068 A1 | 8/2009 | Thomas et al. | |

OTHER PUBLICATIONS

Kuz'Min et al. Magnetic therapy apparatus with adaptable electromagnetic spectrum for treatment of prostatitis and gynecopathies. Biomedical Engineering, vol. 42, No. 2, 2008, pp. 44-46. URL: http://www.spingerlink.com/contect/q030666176660h77.

D'Ovidio et al. Design and experiment of "U" shaped iron-magnetic guideway interacting with HTS "runner" for lift and guidance of vehcile. The 19th International Conference on Magnetically Levitated Systems and Linear Drives. 2006. p. 4; URL: http://www.maglev2006.com/001_D%27Ovidio_ok/001_D%27Ovidio_ok.pdf.

*Primary Examiner* — Charles A Marmor, II
*Assistant Examiner* — Carrie R Dorna
(74) *Attorney, Agent, or Firm* — Buskop Law Group, PC; Wendy Buskop

(57) ABSTRACT

A magnetic method for therapeutic treatment of an animal with a tissue dysfunction using a pair of very low power electromagnetic coils connected to a pulse generator, a kit using the pulse generator connected to a pair of very low power electromagnetic coils, and a pet bed containing the pair of very low power electromagnetic coils and pulse generator. The pulse generator can include a power supply, a bi-directional communication and power port, a microcontroller, a processor, a data storage, computer instructions, transistors, a voltage multiplier, and power supply conduits.

29 Claims, 12 Drawing Sheets

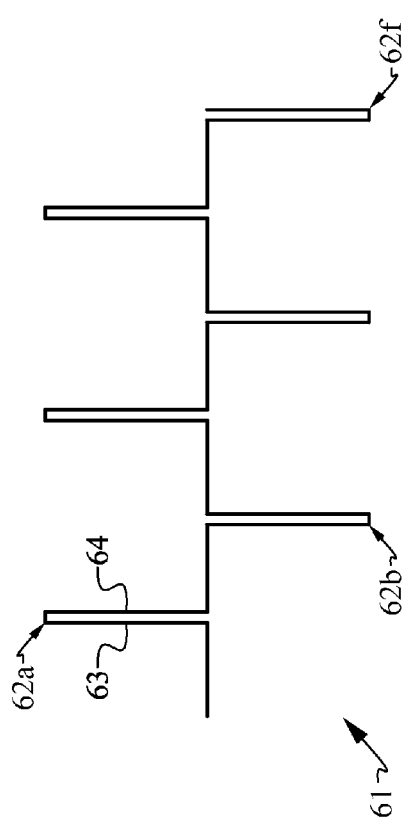
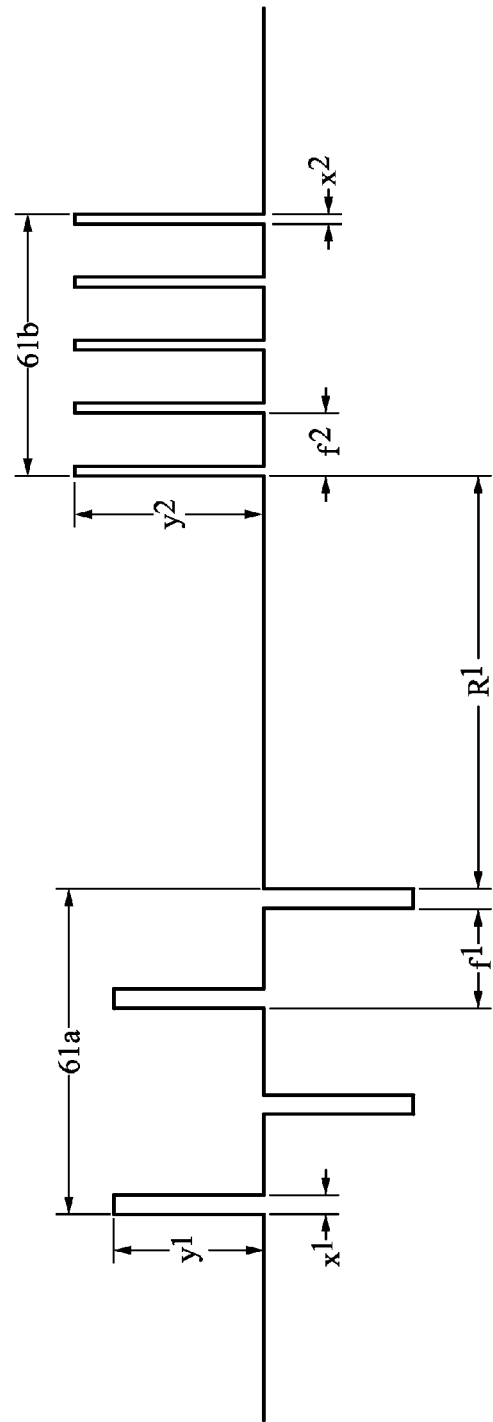
FIGURE 1
FIGURE 2

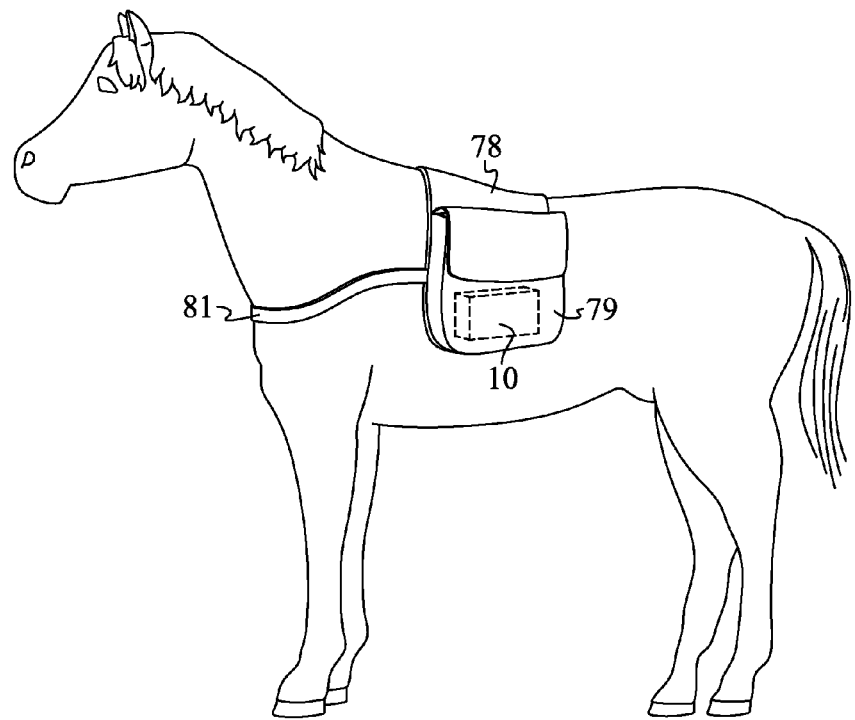
FIGURE 8A
FIGURE 8B
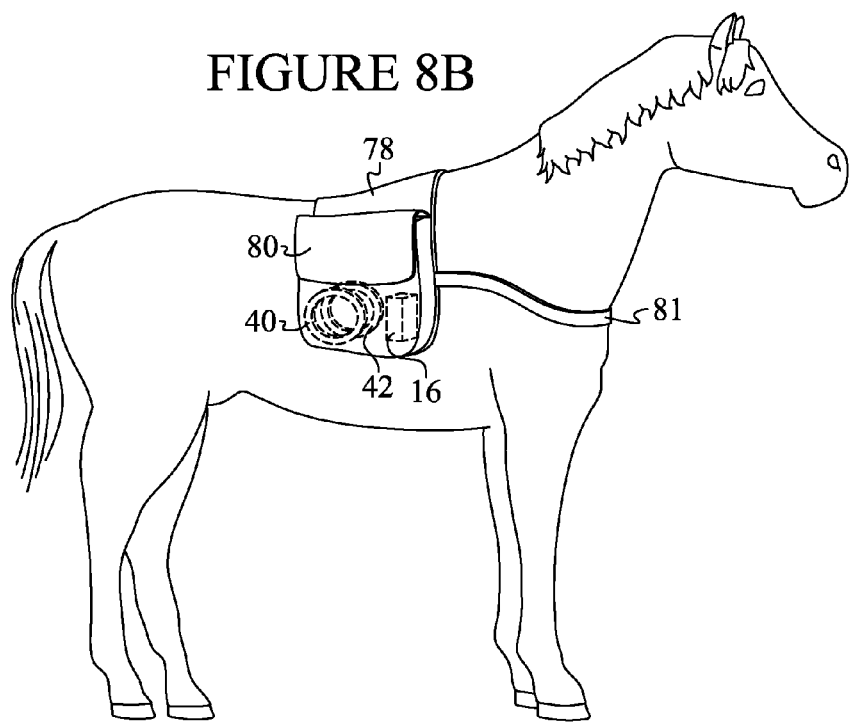

```
                                    ┌─────┐
                                    │ 10A │
                                    └──┬──┘
┌─────────────────────────────────────────────────────────────────────┐
│  GENERATING PULSE BLASTS IN CONTROLLED SEQUENCES TO                 │
│  PRODUCE A PLURALITY OF ELECTROMAGNETIC FIELD                       │──707
│  VECTORS THAT TRANSLATE THROUGH SPACE PROXIMATE                     │
│  THE ELECTROMAGNETIC ARRAY OVER TIME                                │
└─────────────────────────────────────────────────────────────────────┘
```

| |
|---|
| GENERATING PULSE BLASTS AT RANDOM INTERVALS WITHIN SPECIFIED RANGES OF PULSE PARAMETERS USING COMPUTER INSTRUCTIONS IN THE DATA STORAGE TO INSTRUCT THE PROCESSOR — 708 |
| PRODUCING UNIPOLAR ELECTROMAGNETIC PULSES WITH LEADING EDGE ELECTROMAGNETIC SLEW RATES GREATER THAN 200 KG/S AND TRAILING EDGE MAGNETIC SLEW RATES LESS THAN 200 KG/S AND USING PULSES WITH A DURATION LONGER THAN 200 MICROSECONDS — 709 |
| ADJUSTING PULSE PARAMETERS TO STIMULATE EXTRACELLULAR SIGNALS, TRANS-MEMBRANE SIGNALS, INTRACELLULAR SIGNALS, OR COMBINATIONS THEREOF — 710 |
| ADJUSTING PULSE PARAMETERS TO SIMULATE A COMBINATION OF SIGNALS ASSOCIATED WITH AT LEAST ONE MEMBER OF THE GROUP CONSISTING OF: EXTRACELLULAR SIGNALS ASSOCIATED WITH MECHANICAL LOADING OF THE TARGET TISSUE; TRANS-MEMBRANE SIGNALS ASSOCIATED WITH MECHANICAL LOADING OF THE TARGET TISSUES; AND INTRACELLULAR SIGNALS ASSOCIATED WITH MECHANICAL LOADING OF THE TARGET TISSUES — 711 |
| EMPLOYING PULSES WITH RANDOMIZED PULSE PARAMETERS TO PREVENT PHYSIOLOGICAL ACCOMMODATION OR NEURAL ACCOMMODATION FOR TREATMENT OF CHRONIC PAIN, ACUTE PAIN, OR COMBINATIONS THEREOF — 712 |

FIGURE 10B

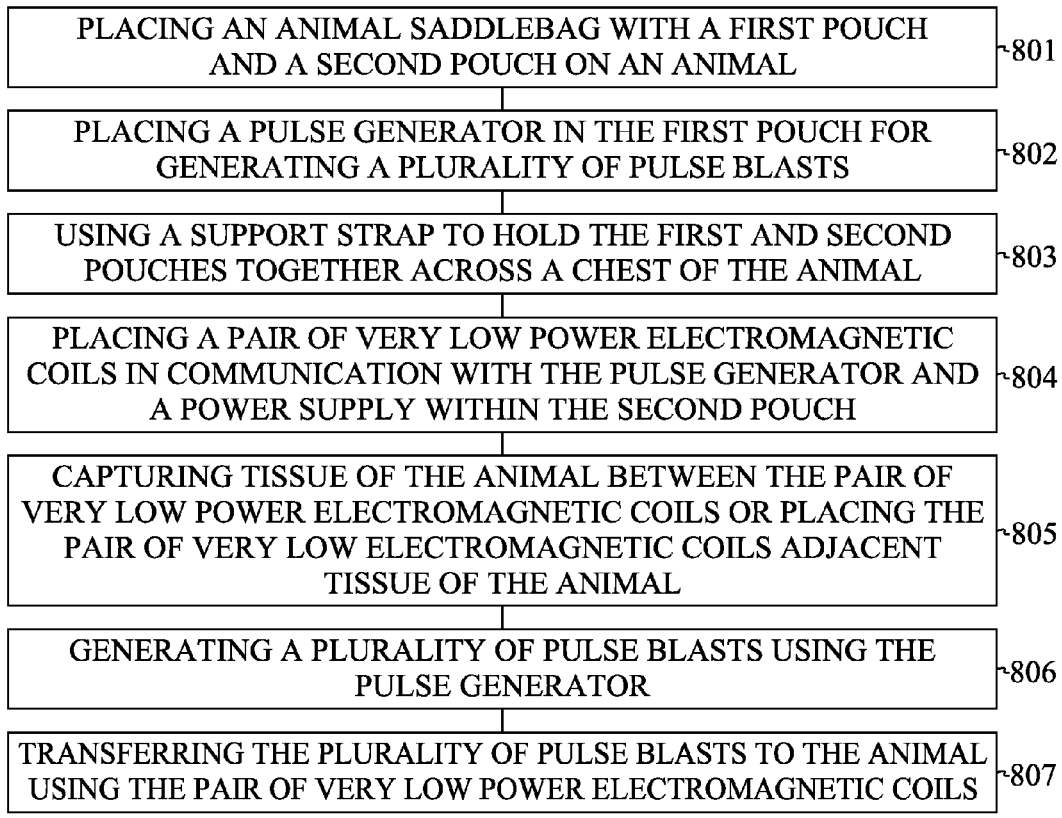
FIGURE 11
FIGURE 12
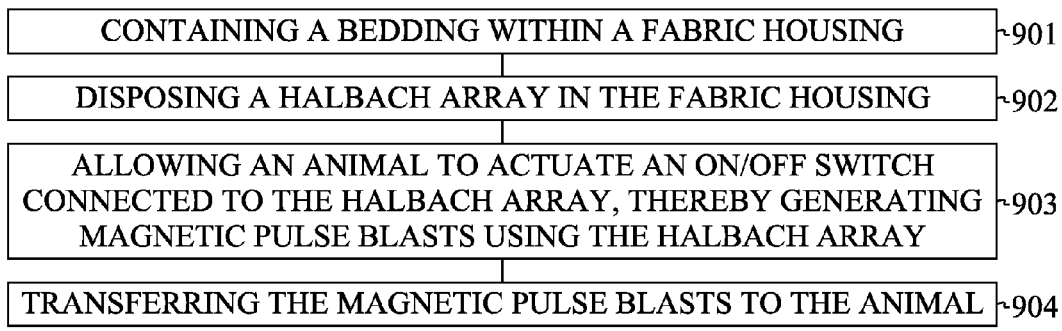

MAGNETIC METHOD FOR TREATMENT OF AN ANIMAL

CROSS REFERENCE TO RELATED APPLICATION

The present applications claims priority and the benefit of U.S. Provisional Patent Application Ser. No. 61/265,720 and U.S. Provisional Patent Application Ser. No. 61/265,716 filed on Dec. 1, 2009. These references are incorporated in their entirety.

FIELD

The present embodiments generally relate to a method for therapeutically treating afflicted tissue and cells of animals using electromagnetic fields.

BACKGROUND

A need exists for a method for therapeutic treatment of afflicted tissue and cells of animals that is non-invasive, easy to apply, and quick to provide relief.

The present embodiments meet these needs.

BRIEF DESCRIPTION OF THE DRAWINGS

The detailed description will be better understood in conjunction with the accompanying drawings as follows:

FIG. 1 is a diagram of bipolar square-wave pulses produced with a pulse generator.

FIG. 2 is a diagram showing a pulse blast.

FIG. 8A is an animal wearing a kit.

FIG. 8B is a view of the opposite side of the animal in FIG. 8A.

FIG. 11 is a diagram of another embodiment of the method.

FIG. 12 is a flow diagram of another embodiment of the method.

Figure 3:
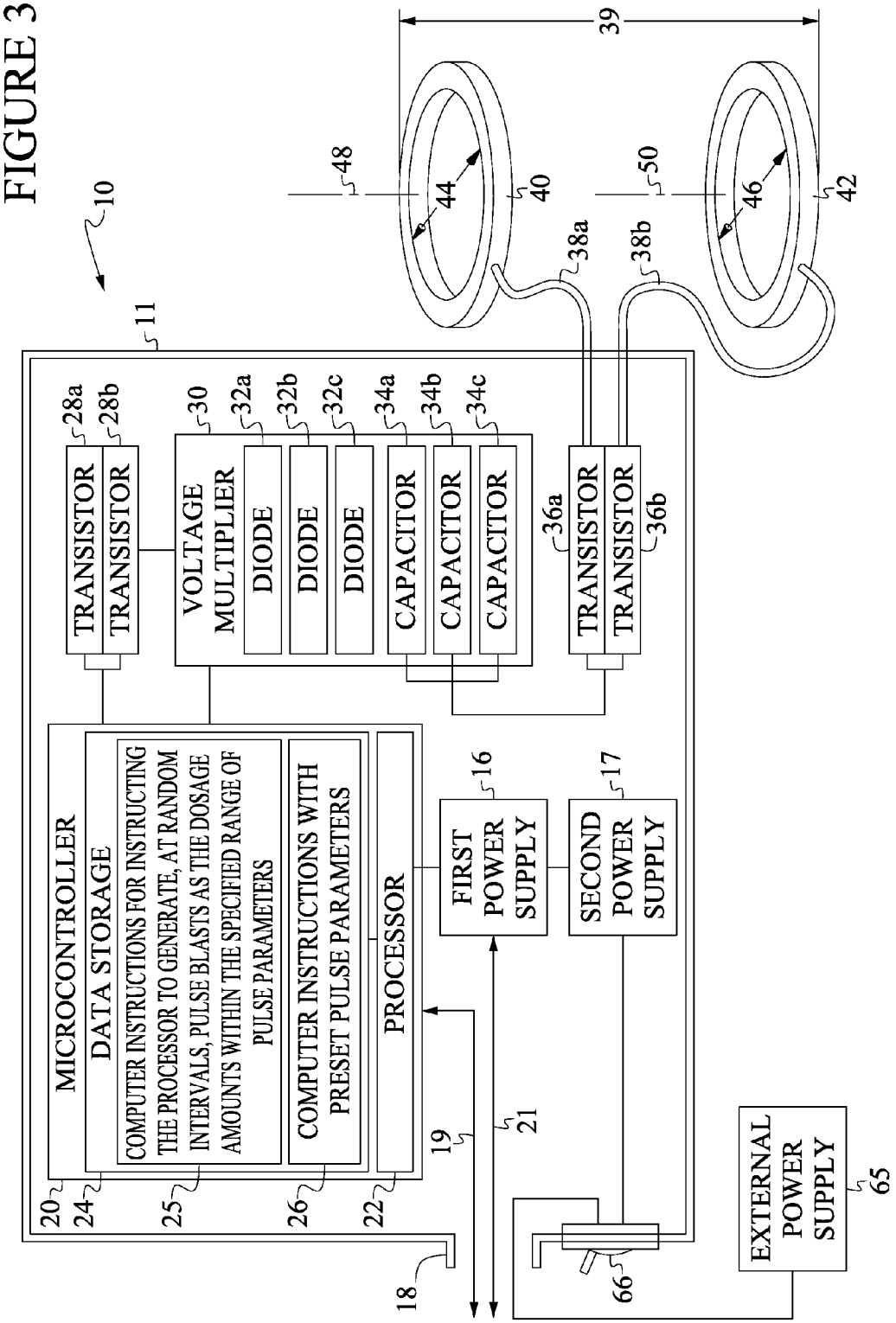
FIG. 3 is a diagram of the pulse generator.

The present embodiments are detailed below with reference to the listed Figures.

DETAILED DESCRIPTION OF THE EMBODIMENTS

Before explaining the present method in detail, it is to be understood that the method is not limited to the particular embodiments and that it can be practiced or carried out in various ways.

The present embodiments relate to a therapeutic method for treating various ailments, or injuries, such as osteoarthritis and other conditions that relate to pain of the joints, bones, or tissues of the musculoskeletal system, the tissues and structures of the cardiovascular system, the skin, and the central and peripheral nervous systems.

Various terms are used herein with particular meanings

The term "pulse blast", as used herein, refers to pulse blasts that can have from about 1 pulse to about 100 pulses contained within each pulse blast from very low power electromagnetic coil pairs. The pulse blasts enable the very low power electromagnetic coil pair to affect tissue and perform various functions.

Pulse blasts can be formed using pulses that are not sine-waves, but are arbitrarily-shaped waves of electrical energy to electromagnetic coils. The waves can be in an embodiment, square-waves of electrical power.

The arbitrarily shaped waves are delivered to electromagnetic coils, resulting in an induced electromagnetic pulse with desired pulse parameters that penetrates tissue that is disposed between or near the electromagnetic coils. Each arbitrarily shaped wave of electrical energy has a leading edge, a trailing edge or combinations of both edges.

Pulse blasts in an embodiment can be a series of single pulses.

The term "pulse", as used herein, refers individual pulses that are created and contained within each pulse blast. A single pulse or alternatively, multiple pulses can be used to form a pulse blast, however, each pulse must have either a trailing edge, a leading edge or both trailing and leading edges to be usable herein.

Each pulse, when graphed, can have units of time as the x-axis and amplitude in Gauss as the y-axis for each pulse shape. The pulses are generated by a very low power pulse generator such as one actuated by a 9-volt battery.

The pluses can have one of a variety of different shapes. Each electromagnetic pulse can be shaped over time, such as in microseconds, to approximate a shape, such as a trapezoid, a polygon, a triangle, a Gaussian function, a Dirac delta function or combinations of these shapes. The shapes can also be square. The amount of time can be a few microseconds, such as 10 microseconds to 100 microseconds, 10 microseconds to 200 microseconds, or 10 microseconds to 1000 microseconds.

Each shaped electromagnetic pulse is generated having a leading edge or trailing edge slew rate of at least 200 kiloGauss/second for at least a duration from 0.1 microseconds to 1000 microseconds without forming a sine shaped pulse wave. The term "power supply", as used herein, refers to the use of batteries, line power from a wall outlet transformed into DC power at a suitable voltage, or other suitable sources of electrical energy.

The power supply is used to operate a microcontroller that in an embodiment can automatically sequence between predetermined sequences of pulses for predetermined intervals of time.

The term "bi-directional communication and power port" refers to connectors such as a D-subminiature 9-pin connector, stereo audio cable connectors, or other suitable electronic connectors The term "communication signal" refers to signals used to drive a voltage multiplier, to energize electromagnetic coils, or to provide a signal to reprogram a microcontroller.

The term "microcontroller" refers to any commercially available suitable low voltage microcontroller, microprocessor, or other programmable electronic device.

The term "low voltage" refers to a voltage from about 1 volt to about 80 volts. In an embodiment, a 9-volt battery can be used to power the microcontroller that provides the electromagnetic pulse bursts through at least one pair of wires to the electromagnetic coils which can be used in a stacked arrangement, a "FIG. 8" arrangement, a sandwich arrangement with the tissue for therapy treatment located between the coils or a side by side parallel arrangement.

The term "low amperage" refers to amperages of less than 1 amp and greater than 0.001 amps, during the generation of stimulation pulses where amperage is averaged over a period of at least 10 seconds.

The term "low power" refers to the product of one of the voltages from the range of low voltages with one of the amperages from the range of low amperages.

The microcontroller uses pulse parameters of at least one pulse blast that can simulate a signal that includes an extracellular signal associated with mechanical loading of a target tissue, trans-membrane signals associated with mechanical loading of a target tissue, intracellular signals associated with mechanical loading of a target tissue, or signals associated with nerve synapse signals to a target tissue, or combinations thereof.

The term "processor" refers to a component within a microcontroller that makes computations and decisions and is capable of determining precise values of time and logic states for driving the elements of the pulse generator. The microprocessor should be capable of comparing a first set of signals to predetermined values stored in an associated data storage in communication with the processor.

The term "data storage" refers to a flash memory, a removable jump drive, a hard drive, or a portion of the microcontroller that is either within or outside of the microcontroller that allows software, firmware, and data to be stored, recalled, modified, and executed therefrom.

The term "computer instructions with preset pulse parameters" refers to computer instructions that define an exact nature of the pulse blasts to be delivered from a pulse generator, or a range of values for each simulation parameter from within which the specific pulse parameter values may be either deterministically, pseudo-randomly or randomly selected.

As the term is used herein, "vectors" refers to a mathematical representation of a magnetic field which contains quantitative information about both the magnetic field direction and the field amplitude or strength.

The term "normal-to plane axis", as used herein, refers to an axis that is perpendicular to a plane surface of an individual coil or a coil array encapsulated within a flexible polymer. For example, if the electromagnetic coil is elliptical, the plane surface would be the plane of the first surface of the elliptical shaped electromagnetic coil. For complex shapes of coils that are bent or shaped in three-dimensions, this term is to be interpreted as an approximation of the coil geometry as essentially planar on average, or for a sufficiently small area of the coil under consideration to approximate a planar geometry.

The term "mechanically flexible polymer coating", as used herein, refers to a flexible, bendable, not brittle coating that can contain an elastomeric material such as silicone, urethane, or a thermoplastic elastomer compound.

In embodiments, the mechanically flexible polymer coating can be a washable, heat resistant thin coating of a polymer such as a polypropylene homopolymer, a polypropylene copolymer, or a cross linked polymer of polypropylene and polyethylene, forming a bendable, impact resistant, coating over the electromagnetic coils such as coatings used to encapsulate electrical wires.

The mechanical flexible polymer coating can be a laminate with a first coating covering a second coating that encapsulates the electromagnetic coils while allowing the electromagnetic coils to be flexed and bent into a desired shape.

The coating can be manufactured to incorporate colors or physical textures or both that enable the user to correctly identify, align and place the coils during use. Antibiotics or a similar beneficial coating commonly used on medical devices that come into contact with the skin can also be incorporated into the coating.

The term "computer instructions in the data storage for instructing the processor to generate random pulse blasts, random pulses, or randomization of selected pulse parameters according to a random pulse generator, as the dosage amounts within the specified range of pulse parameters" refers to a series of algorithmic computer codes that can allow the pulse generator to sequentially generate pulses or pulse blasts with a predetermined number of pulses in the pulse blasts and having a predetermined time interval between the pulse blasts or pulses, with any of the pulse parameters being varied within specified limits. In embodiments, a random number generator can be used to generate variable pulse blasts in the dosage amounts.

The phrase "saddlebag" refers to a single pouch or a configuration of two pouches connected together which can reside on a back of an animal. The saddle bag can have a first pouch riding on a first side of an animal connected to a second pouch riding on a second side of the animal, so as to allow for safe carriage of the power supply and the pulse generator by an animal. A support strap can wrap around the front or chest area of the animal enabling the two pouches to stay securely on the animal for therapeutic purposes.

As this term is used herein, the "magnetic Halbach array" can be an array of magnetic elements in a one-dimensional (linear) or a two-dimensional (planar) array wherein in-plane magnetic field generators reside in the magnetic Halbach array and can act to produce large amplitude magnetic fields on one side of the magnetic Halbach array, while producing a minimal magnetic field on the other side of the magnetic Halbach array.

The term "animal actuated on/off switch" refers to a simple mechanical pressure switch, an optical detector switch, a heat detector switch, a motion detector switch, a capacitance proximity detector switch, a sound or vibration detector switch, an ultrasonic detector switch, or similar means by which the presence of an animal can be established and detected by the microcontroller.

The term "heating element" refers to an electrical element that allows the generation of controlled heat which can be applied to pet bedding.

The term "cooling element" refers to an electrical element such as an array of Peltier devices, which allow heat to be removed from part or all of a pet bed or other animal bedding.

The term "physiological accommodation", which also includes the more specific term "neural accommodation", refers to the tendency of cells and tissues, when subjected to the same stimulus signal over time, to become increasingly less responsive to that signal over time.

The terms "randomization of stimulation parameters" and "variation of stimulation parameters" refer to the alteration of stimulation parameters within defined limits to overcome the undesirable effects of physiological accommodation and neural accommodation, while continuing to elicit the desired response from the cells or tissues being stimulated.

The term "electromagnetic acupuncture" refers to the use of the coils to focus electromagnetic stimulation at one or more specific anatomic regions as an alternative approach to achieve the results of traditional acupuncture without the use of traditional acupuncture needs or similar devices.

The coils can be magnetic coils or electromagnetic coils.

Embodiments can be used for treatment of a cellular dysfunction of tissue or an extracellular matrix disruption of a tissue, or both of these problems, and can use a pulse generator and at least one pair of electromagnetic coils.

In one or more embodiments, the electromagnetic coils can be disposed adjacent to a site of cellular dysfunction or adjacent to a site of tissue having an extracellular matrix disruption. For example, the electromagnetic coils can be placed side-by-side to allow treatment of tissues that are thick or otherwise difficult to access on both sides.

As another example, the coils can be stacked together to functionally form one stack which can then be placed over a location on the body, such as an organ, and used in a manner similar to electromagnetic acupuncture to treat one location on the surface of the body or in deeper tissue below the coil stack. Multiple individual coils or multiple stacks of coils can be used to simultaneously treat multiple locations in a manner similar to electromagnetic acupuncture at several location sites.

Embodiments can also be used to accelerate healing of bone, skin, nerves, and other cells and tissues of the musculoskeletal system, the central or peripheral nervous system and the cardiovascular system.

Embodiments can be used to promote the healing of refractory or non-healing bone fractures; to reduce swelling from osteoarthritis or rheumatoid arthritis; to reduce scar tissue formation in skin, tendons, muscles, ligaments, nerve and cardiovascular tissues; to reduce infection rate; and to promote increased joint range of motion subsequent to injury or a degenerative disease.

Embodiments can be used to treat or reduce pain including: idiopathic joint pain, pain associated with fibromyalgia, lower back pain, compartment pain, referred pain, acute pain, chronic pain, and migraines.

Embodiments can be used to treat strains of muscles, tendons, ligaments, bulging or damaged vertebral disks, osteopenia, temporomandibular joint, and craniofacial structures.

Embodiments can be used to treat: critical defects in bone; injured cardiovascular tissues; heart failure; heart injury by reducing monocyte-induced swelling; spinal cord injury by promoting nerve re-growth, fibroblast infiltration and growth, and scar formation; nerve injury; nerve degeneration; loss of bladder or bowel control; neurogenic incontinence; neurogenic erectile dysfunction; ulcers; injury to the rotator cuff; internal organ disorders including liver, pancreas, kidney and lung disease; tremors associated with Parkinson's disease, ataxia, or multiple sclerosis; neuro-developmental and neurodegenerative diseases, mild to severe brain ailments, disorders of the central nervous system (in primates), non-responsive wounds including diabetic foot ulcer and post-surgical abdominal ulcer; cancer by inhibiting tumor formation and growth; infections generating a bacteriostatic field at a site of injury.

Embodiments can be used to improve outcome and to accelerate healing after surgery or injury of the cornea and corneal implants, engraftment of surgical implants, ejection fraction after surgery for heart failure; cardiac muscle regeneration; functional outcome after heart surgery as measured by a predetermined walk, blood flow in ischemic limbs; limb salvage after removal of blood flow; or strength of tissues following injury.

Embodiments can also be used to decrease cardiac scarring after heart failure or surgery; accelerate nerve regeneration; treat strokes by improving blood flow to the affected areas of the brain; reduce functional loss following a stroke; and recover tone of the muscles of the urogenital system.

Embodiments can be used as an adjunct to stem cell therapy to improve engraftment; for in vivo amplification of stem cells, to accelerate phenotypic development of the stem cells into the desired tissue phenotypes, for targeting engraftment, and for guiding phenotypic development into the desired tissue types.

The pulse generator can generate a plurality of pulse blasts. Each pulse blast can be formed from one or more pulses. The pulse generator can have at least one power supply such as one or more connected batteries or a battery and a battery charger.

An electrical current can be generated by the power supply or the pulse generator. The power supply can be from a 110 or 220 line voltage that is stepped down to provide the very low power needed for the electromagnetic coil pairs.

The pulse generator can have a bi-directional communication and power port for flowing power into and out of the pulse generator and flowing communication signals into and out of the pulse generator.

The pulse generator can have a microcontroller in communication with the bi-directional communication and power port.

The microcontroller can have a processor that can be in communication with the power supply. Data storage can be in communication with the processor and computer instructions with preset pulse parameters or ranges of pulse parameters can be stored in the data storage.

A pair of first transistors can be in communication with the microcontroller. In embodiments, multiple pairs of first transistors can be in communication with the microcontroller.

The first pair of transistors can allow the microcontroller to control power flow into the voltage multiplier or other voltage amplification or voltage conversion device.

A voltage multiplier can be connected to the at least one pair of first transistors. The voltage multiplier can include one or more diodes and one or more capacitors. The voltage multiplier can include combinations of diodes and capacitors for communication with the microcontroller for increasing or decreasing the output voltage of the pulse generator.

In embodiments, the diodes can be rapid switching diodes, and the capacitors can be surface mount ceramic capacitors.

In embodiments, the voltage multiplier can be a Villard Cascade Voltage Multiplier, though other configurations to achieve the desired voltage may be employed.

The pulse generator can have a pair of second transistors in communication with the voltage multiplier to form an output stage. In embodiments, the pulse generator can have multiple second transistors. The second transistors can be controlled by the microcontroller to form an electronic signal to send to a coil, a pair of coils, or Helmholtz-like magnetic array to form a plurality of pulse blasts or pulses.

In embodiments, the second transistors can allow a microcontroller to control electrical energy flow from the pulse generator to the electromagnetic coils; thereby controlling pulse parameters.

Embodiments can further include a pair of power supply conduits, which can be wires that each connect to at least one of a pair of electromagnetic coils. The pair of power supply conduits, such as those connecting the power supply to the pulse generator, or connecting the pulse generator to the electromagnetic coils, can be wires.

Embodiments can include at least one very low power electromagnetic coil pair sized to generate a plurality of pulse blasts which can have a slew rate of at least 200 kiloGauss per second (kG/s).

Each very low power electromagnetic coil pair can have a first electromagnetic coil with a first electromagnetic coil diameter and a first electromagnetic coil axis.

The first electromagnetic coil first side can have a first polarity, and a first electromagnetic coil second side can have a second polarity. The first electromagnetic coil can connect to one of the pair of power supply conduits.

The very low power electromagnetic coil pair can have a second electromagnetic coil with a second electromagnetic coil diameter and a second electromagnetic coil axis.

A second electromagnetic coil first side can have a first polarity, and a second electromagnetic coil second side can have a second polarity. The second electromagnetic coil can connect to one of the power supply conduits.

The first electromagnetic coil can be disposed opposite the second electromagnetic coil, enabling a Helmholtz-like, very low power electromagnetic coil pair to treat tissue placed between or proximate the first electromagnetic coil and second electromagnetic coil and their associated pulse blasts.

For the embodiment having Helmholtz-like electromagnetic coil pairs, the first electromagnetic coil and the second electromagnetic coil can be disposed at separations from about 0.1 radius to about 20 radii.

The first electromagnetic coil and the second electromagnetic coil can be oriented so that when the coils are energized using the pulse generator, a plurality of electromagnetic wave pulses can be generated with slew rates of at least 200 kG/s for at least a duration about 0.1 microsecond to about 200 microseconds and these pulses can be generated to have different wave shapes.

Each electromagnetic wave pulse can have a leading edge and a trailing edge. Each leading edge to trailing edge can have a duration of about 0.1 microsecond to about 200 microseconds.

In embodiments, pulse parameters controlled by the microcontroller can include a pulse voltage or current, a pulse duration, a pulse polarity, a number of pulses per unit of time; a number of pulses per pulse blast, a time duration between pulses in each pulse blast, a time duration between pulse blasts, or combinations thereof.

In embodiments, the pulse voltage can range from about 5 volts to about 200 volts.

In embodiments, the pulses can be bipolar pulses.

In embodiments, an external power supply, such as a 110 volt wall outlet or a generator, can be connected to the power supply to allow for uninterrupted pulse blast generation for a dosage amount of time. The external power supply can also be a single battery or a plurality of connected batteries. The pulse generator can have an on/off switch for actuating the external power supply to supply power to the pulse generator.

The external power supply can be one or more DC batteries, such as four "C" batteries, two or more "AA" batteries, or one or more 9-volt batteries. The pulse generator can be run on 110 volts of power provided that there is a current conditioning device secured to the generator. In one or more embodiments, the pulse generator can run on 220 volts AC. For example, the pulse generator can be configured to be operated using common United States line voltage or common European line voltage.

In embodiments, between about two transistors to about forty transistors can be utilized external to the microcontroller. The capacitor and the first and second transistor pairs can be connected together in an H-bridge configuration.

The microcontroller can include computer instructions, such as a soft remote terminal unit instruction, allowing the microcontroller to be reconfigurable on-line, without any down time of the pulse generator. The pulse generators of an array of pulse generators can be reconfigured on-line using communication from an administrative server in communication with the pulse generators through a network which can be a wireless network.

Each pulse blasts can be composed of positive polarity pulses, negative polarity pulses, or combinations thereof. The pulse blasts can include different numerical quantities of pulses. Differing intervals of time can occur between pulse blasts The alignment of the axis of each electromagnetic coil can range from being parallel and coaxial to being anti-parallel, adjacent, and coplanar. Each pair of electromagnetic coils can be stacked together or separated by a distance between the coils sufficient to allow the affected tissue to be located between the coils.

A plurality of the pairs of electromagnetic coils can be formed into an electromagnetic array with a common controller for treating a large area of tissue. The electromagnetic array can be formed to surround an entire limb.

The electromagnetic array can generate pulses in controlled sequences to produce a plurality of magnetic field vectors that rotate through a space proximate to the electromagnetic array over a preset unit of time and/or that translates through the space near the electromagnetic array over time.

The electromagnetic array can be a set of electromagnetic coils arranged in such a manner as to allow one common controller to energize or de-energize any combination of electromagnetic coils in the magnetic array; thereby allowing the common controller to control the resulting electromagnetic field within and near the electromagnetic array.

The common controller of the electromagnetic array can be a microcontroller which controls the pulse generator to generate pulses or pulse blasts which can be communicated to a pair of electromagnetic coils or an electromagnetic coil array.

The plurality of electromagnetic coils can be arranged into a member of the group consisting of: a two dimensional Halbach array, a one dimensional Halbach array, and combinations thereof.

At least one pair of electromagnetic coils of each Halbach array can have an in-plane axis to act as a flux conduit between a normal-to-plane axis of at least one other pair of electromagnetic coils.

Each Halbach array can contain flux concentrators of iron, ferrite or similar magnetic material to concentrate the magnetic field at specified points within each Halbach array.

The distance between the pairs of electromagnetic coils in each Halbach array can be adjusted to range from about 0.5 inches to about 10 inches, measured as the center-to-center distance between the normal-to-plane axis.

Each Halbach array can be sealed within a mechanically flexible polymer coating, which allows for the generation of electromagnetic fields to be unimpeded. Each Halbach array can be mechanically flexible and conformable to adapt to a curvature of an anatomic surface of a head, a neck, a torso, a pelvis, a limb, or combinations thereof.

In embodiments, additional computer instructions can be in the data storage of the pulse generator for instructing the processor to generate, at random intervals, pulse blasts or pulses as the dosage amounts within the specified range of pulse parameters. Pulses with a duration longer than about 200 microseconds can be used to produce pseudo-unipolar magnetic pulses.

The pair of electromagnetic coils can be coils readily formed from multiple turns of suitable electrical wire or another form electrical conductor. The electromagnetic coil diameters can be measured as the average diameter across any of the electromagnetic coils. Each electromagnetic coil can have an axis that is perpendicular to the plane in which the electromagnetic coils are wound, and through the center of each electromagnetic coil.

In embodiments, the very low power electromagnetic coil pair can be defined to be a configuration of two short electrical solenoids coils that are magnetically aligned north-to-south on the same axis and separated by some distance. The distance of separation can be adjusted to accommodate the shape, thickness, and physical disposition of the tissue to be treated and the surrounding tissues and anatomical structures, but only when the distance between the coils is not limited.

The plurality of electromagnetic pulses can be generated as a result of the electrical energy discharged through each of the electromagnetic coils as the pulses are originated from the pulse generator.

Cellular Dysfunction

The pulse blasts can be used to treat cellular dysfunction of tissue placed proximate to the first electromagnetic coil and the second electromagnetic coil, such as skin tissue that has a cellular dysfunction of a non-healing ulcer and the coils are stacked one on top of the other and wherein one coil is touching a bandage over the non-healing ulcer.

Pulses for this cellular dysfunction are generated as a trapezoidal wave pattern with at least a trailing edge and a leading edge at a first cycle of 10 bipolar pulses per second with each pulse having a duration of 100 microseconds for a period of 10 minutes, then a second cycle of a burst of 5 pulses in 100 milliseconds followed by a delay of $9/10^{th}$ of a second during which there are no pulses, after which this cycle is repeated for 10 minutes.

Extracellular Matrix Disruption

The pulse blasts can be used to treat an extra cellular matrix disruption of tissue, such as a partial thickness tear of the Achilles tendon of a primate.

The therapy would involve using the first electromagnetic coil and the second electromagnetic coil forming a very low power electromagnetic coil pair disposed on opposite sides of the tendon injury. The coils can each be touching the skin or can be separated from the skin by a bandage or wound dressing.

Pulses for this extracellular matrix disruption are generated as Dirac delta function patterns with at least a trailing edge and a leading edge at a first cycle of 10 bipolar pulses per second continuously for 30 minutes, followed by 20 minutes of rest, and thereafter the stimulation and rest pattern is repeated for the duration of the therapy, for example: 8 hours per day each day for 4 weeks.

Tissue Injury

The pulse blasts can be used to treat a tissue injury afflicting tissue, such as a myocardial infarction, when the very low power electromagnetic coil pairs are formed in a "figure 8" pattern and the very low power electromagnetic coil pairs are placed on the chest within 1 inch and 8 inches of the afflicted tissue for the heart.

Pulses for this tissue injury are generated as square wave patterns with only a sharp leading edge at a rate of 200 kilo/Gauss per second and a trailing edge of a rate of 10 kilo/Gauss per second. The heart tissue would be exposed to this wave pattern for up to 24 hours per day for up to 2 weeks as the therapy dose.

Tissue Degenration

The pulse blasts can be used to treat a tissue degeneration afflicting tissue, such as an age-related degeneration of central nervous tissue.

For this therapy, electromagnetic coils are formed with a first electromagnetic coil on one side of an animal skull, such as a dog and the second electromagnetic coil on the opposite side of the dog skull. For this therapy, four pairs of very low power electromagnetic coils can be used with a central controller powered by a group of three 9-volt batteries.

Pulses for this tissue degeneration therapy are generated as a bipolar polygon wave pattern at a rate of 5 pulse blasts per second for 1 hour once per 24 hours. To prevent neural accommodation, the pulse parameters are varied pseudo-randomly within a specified range. Pseudo-random numbers are generated during treatment by the microcontroller within the stimulator pulse generator. These numbers are used in an algorithm to vary the pulse frequency over the range of 3 pulses per second up to 20 pulses per second. The variation occurs once every minute. Pulse polarity is also reversed at pseudo-random intervals.

Pain in Tissue—Acute or Chronic Pain

The pulse blasts can be used to treat chronic or acute pain.

Pain From Tissue Degeneration

In this treatment, tissue such as a joint in a horse leg may cause osteo-arthritic pain due to joint degeneration and it can be treated.

Each electromagnetic coil is placed on the skin adjacent the joint. The joint can be sandwiched between the two coils. Each very low power electromagnetic coil pair can be a 50 millimeter diameter coil.

Pulses for treating this elbow pain are generated as triangle wave patterns with at least a trailing edge.

The triangle wave patterns are generated as unipolar pulses which alternate polarity between cycles. Each pulse can last 100 milliseconds.

In a first cycle, the electromagnetic coils can generate a "north" magnetic pole blast followed by a second cycle having a "south" magnetic pole pulse blast, which is again followed by a third cycle of "north" magnetic pole blasts.

The three cycles are repeated over a period of 90 minutes.

Pain From Tissue Injury

For the pain known as "acute" pain due to a broken femur.

The coils are placed flat on one side of the leg, with the first electromagnetic coil adjacent the second electromagnetic coil.

Pulses for this pain are generated as Gaussian function wave patterns with both a leading edge and a trailing edge.

A series of individual bipolar pulses generated at 10 Hertz are generated for 30 minutes. The therapy then continues with 20 minutes of rest without stimulation, and then the pattern of individual bipolar pulses is repeated for the duration of the therapeutic dose.

Pain From Extracellular Matrix Disruption of Tissue

In this treatment, the tissue with extracellular matrix disruption causing pain such as degeneration of at least one spinal disc is treated.

An electromagnetic coil stack of four coils is placed directly on the skin of the lower back proximate to the degenerated spinal disc.

Pulses having a wave shape that is approximately square are generated as a group of six bursts, each having a duration of 5 milliseconds, and then a rest period of 120 milliseconds. This therapy cycle is then repeated for 1 hour (60 minutes), once a day for 10 days to reduce swelling, to strengthen adjacent muscles and reduce the pain from the degenerating disc.

Pain Caused By Cellular Dysfunction Of Tissue

In this treatment, the pain caused by cellular dysfunction of tissue such as rheumatoid arthritis is alleviated.

The first electromagnetic coil and the second electromagnetic coil are placed on top of the skin of the hand in a "FIG. 8" pattern with the source of the rheumatoid arthritis pain directly beneath the adjacent coils.

Pulses for this pain are generated as trapezoidal wave patterns at a rate of 1 Hertz of unipolar blasts for 50 minutes followed by 1 Hertz of bipolar blasts for 20 minutes followed by a 10 minute rest cycle, after which the stimulation cycle repeats.

The therapy is repeated until the pain is reduced by at least 50 percent. The therapy can be applied by the patient as needed for the reduction of pain.

Pain of Idiopathic Origin

In this treatment, the pain in shoulder tissue from an idiopathic origin is treated using a first electromagnetic coil disposed on one side of the shoulder with pain and a second electromagnetic coil disposed on the other side of the shoulder with the painful area placed directly between the opposed coils.

Pulses for this therapy are generated as a first group of trapezoidal wave patterns followed by a second group of polygonal wave patterns.

The first group of trapezoidal wave patterns are generated as three pulse blasts over 30 milliseconds, followed by a rest period of 970 milliseconds, then the second group of polygonal wave patterns with both leading and trailing edges are generated as five pulse blasts over 20 milliseconds. This therapy dosage of the two groups with the rest period is then repeated for a period of time such as 60 minutes.

The very low power electromagnetic coil pairs can be used to treat combinations of these types of problems including, cellular dysfunction of tissue, extracellular matrix disruption of tissue, tissue injury affecting related tissue, tissue degeneration affecting related tissue, and pain caused by tissue degeneration, tissue injury, cellular dysfunction of tissue and pain from an idiopathic origin.

The term "pain from an idiopathic origin" as the term is used herein refers to symptomatic pain from an unknown or difficult to diagnose origin.

Embodiments can include a kit for therapeutically treating animal tissue ailments including cellular dysfunction of a tissue or an extracellular matrix disruption of a tissue.

Kit In Saddlebag

The kit can include an animal saddlebag with a first pouch and a second pouch connected by a support strap for holding the first pouch and second pouch together across a chest of an animal. The animal can be a four legged animal, such as a dog, a horse, a deer, or another animal.

A pulse generator can be placed or disposed in one of the pouches. At least one pair of electromagnetic coils can be placed or disposed in another pouch of the saddlebag, enabling the placement of damaged tissue between the electromagnetic coils.

The saddlebag can be used to place the electromagnetic coils adjacent to a site of cellular dysfunction or adjacent to a site of tissue having an extracellular matrix disruption.

Each pair of very low power electromagnetic coils can be connected to the pulse generator through a power supply conduit.

Pet Bed

Embodiments can include a pet bed for therapeutically treating an animal. The pet bed can include bedding contained in a fabric housing. A Halbach array of electromagnetic coils can be disposed in the fabric housing.

An animal actuated on/off switch can be connected to the Halbach array and to the pulse generator.

Magnetic pulse blasts can be generated when an animal actuates the animal actuated on/off switch.

Additionally, the pet bed can contain a heating element connected to a power source of the Halbach array disposed within the fabric housing. The heating element can be controlled by a microcontroller in the fabric housing that can be actuated when the animal engages the animal actuated on/off switch.

The animal actuated on/off switch can be a pressure sensitive switch, a movement sensitive switch, or a heat sensitive switch.

The pet bed can include a cooling element connected to the power source of the Halbach array. The cooling element can be disposed within the fabric housing. The cooling element can be controlled by the microcontroller providing cooling when the animal engages the animal actuated on/off switch.

The pet bed can include pet bedding. Pet bedding can include any of a variety of arrangement of structures which an animal will rest or sleep. For example, a dog bed can have cedar chips as the pet bedding. A horse can have straw as the pet bedding. A cat can have strips of fabric as the pet bedding. The pet bedding can be contained within the fabric housing, such as a corduroy material or canvas, enabling an animal to rest or to sleep.

The electromagnetic coils, the heating and/or cooling elements, and detector switches can be placed within the fabric housing.

Turning now to the Figures, FIG. 1 shows an example of a typical pulse blast 61 that approximates a series of bipolar square-waves 62$a$-62$f$ usable in a pulse blast with a leading edge 63 and a trailing edge 64. Each pulse can have a duration of between about 0.1 microsecond to about 200 microseconds and has at least one edge with a slew rate of at least 200 kG/s.

FIG. 2 shows an embodiment of two pulse blasts. The first blast 61$a$ is shown consisting of four bipolar pulses with an amplitude y1, a duration x1 and a frequency f1. The first blast 61$a$, as illustrated in FIG. 2, is followed by a rest period R1 before the beginning of the second blast 61$b$. The second blast 61$b$ is shown as 5 unipolar pulses with an amplitude y2, a duration x2 and a frequency f2.

FIG. 3 depicts a pulse generator 10 usable in the embodiments. The pulse generator 10 has a housing 11. In the housing 11 are electronics that generate a plurality of pulse blasts. The pulse generator 10 has a first power supply 16 and an optional second power supply 17.

A bi-directional communication and power port 18 flows power 21 into and out of the pulse generator 10, and flows communication signals 19 into and out of the pulse generator 10. The bi-directional communication and power port 18 can be formed in the housing 11 of the pulse generator 10.

A microcontroller 20 is shown in communication with the bi-directional communication and power port 18. The microcontroller 20 has a processor 22 in communication with either the first power supply 16 or the second power supply 17. The microcontroller 20 also has a data storage 24 in communication with the processor 22. In the data storage 24 are computer instructions 26 with preset pulse parameters.

Also shown are computer instructions 25 in the data storage for instructing the processor to generate at random intervals, pulse blasts, pulses as the dosage amounts within the specified range of pulse parameters.

A first pair of transistors 28$a$ and 28$b$ is in communication with the microcontroller 20.

A voltage multiplier 30 is connected to the first pair of transistors 28$a$ and 28$b$. The voltage multiplier 30 has three diodes 32$a$, 32$b$, and 32$c$, as well as three capacitors 34$a$, 34$b$, and 34$c$. The voltage multiplier 30 is in communication with the microcontroller 20 for increasing or decreasing the voltage of electricity of the pulse generator 10.

A second pair of transistors 36$a$ and 36$b$ are shown connected to the three capacitors 34$a$, 34$b$, and 34$c$. The second pair of transistors 36$a$ and 36$b$ form at least one of a plurality of pulses and/or a pulse blast that are emitted by the pulse generator 10.

A pair of power supply conduits 38a and 38b are shown connected to the second pair of transistors 36a and 36b.

A very low power electromagnetic coil pair 39 is connected to the pair of power supply conduits 38a and 38b. The very low power electromagnetic coil pair 39 is sized to generate a plurality of pulse blasts with a slew rate of at least 200 Kilogauss per second (kG/s).

The very low power electromagnetic coil pair 39 is shown with a first electromagnetic coil 40 with a first electromagnetic coil diameter 44 and a first electromagnetic coil axis 48. A second electromagnetic coil 42 is also shown, with a second electromagnetic coil diameter 46 and a second electromagnetic coil axis 50.

FIG. 3 also shows an external power supply 65 connected to the second power supply 17 through an on/off switch 66 to allow for uninterrupted pulse blast generation for a dosage amount of time. The on/off switch 66 allows for actuation of the external power supply 65 to supply power to at least the first power supply 16 or second power supply 17.

Figure 4:
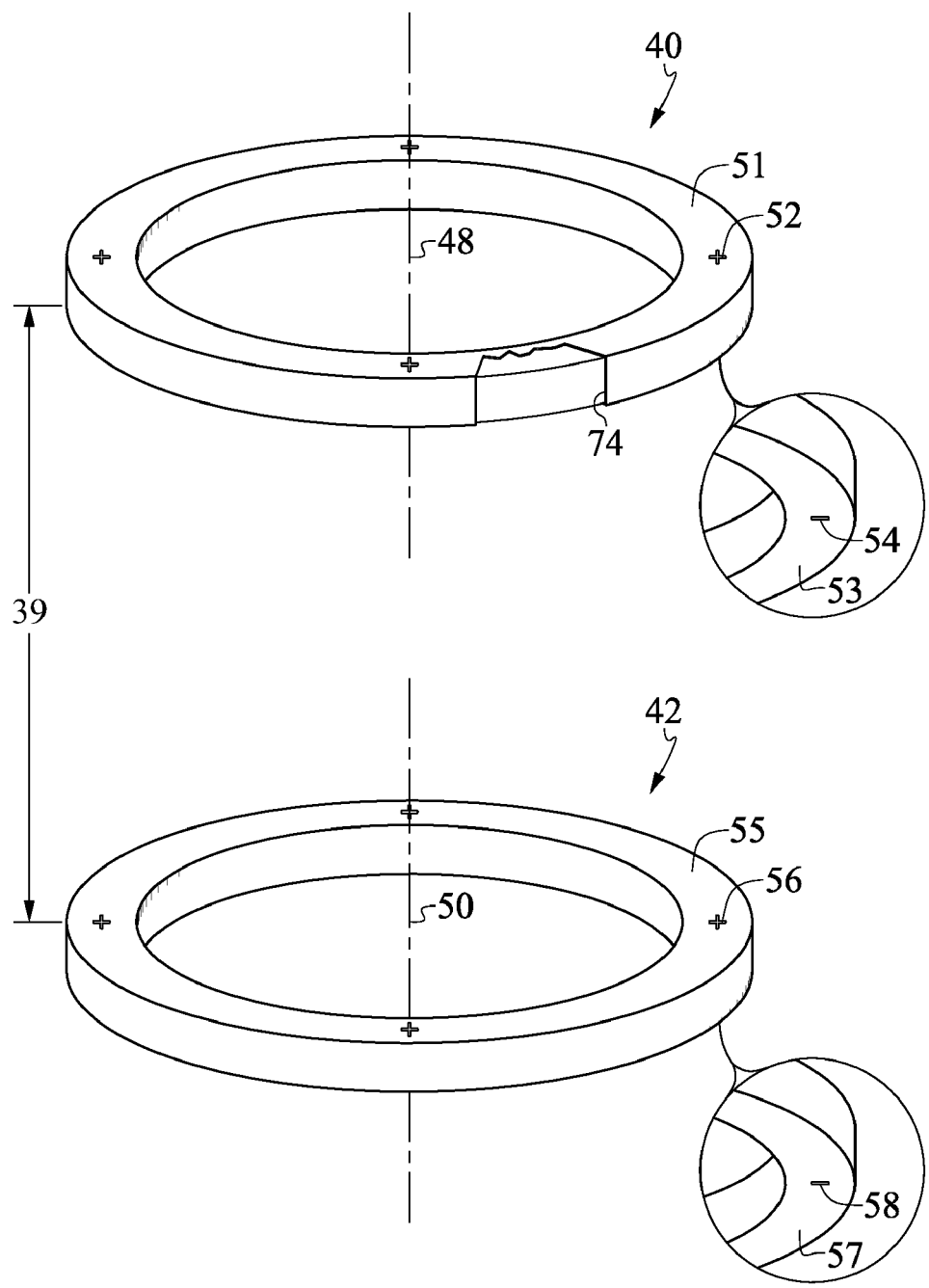
FIG. 4 is a detailed view of two of the electromagnetic coils usable in the method.

FIG. 4 shows a detailed view of the very low power electromagnetic coil pair 39. The first electromagnetic coil 40 with the first electromagnetic coil axis 48 is shown.

A first electromagnetic coil first side 51 with first polarity 52 and a first electromagnetic coil second side 53 with second polarity 54 are shown.

Also shown is a second electromagnetic coil 42 with the second electromagnetic coil axis 50. A second electromagnetic coil first side 55 is shown with a first polarity 56, and a second electromagnetic coil second side 57 is shown with second polarity 58.

FIG. 4 shows that each of the electromagnetic coils can be encapsulated with a mechanically flexible polymer coating 74 which allows unimpeded the generation of the electromagnetic fields.

Figure 5:
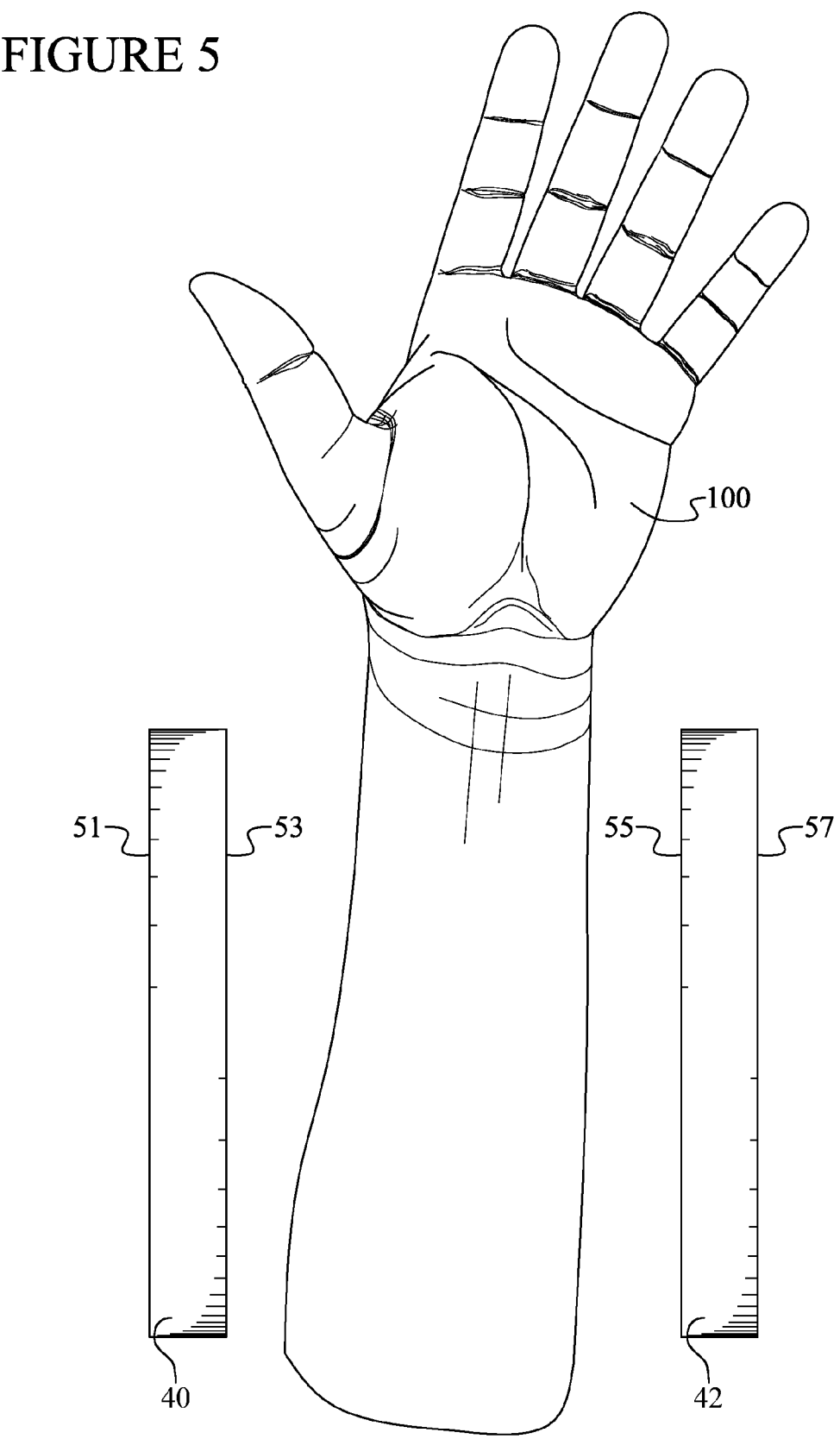
FIG. 5 is a detailed view of an arrangement of electromagnetic coils around a limb.

FIG. 5 shows the orientation of the very low power electromagnetic coil pair for therapeutic treatment. The first electromagnetic coil first side 51 is disposed opposite the second electromagnetic coil second side 57 for treatment of cellular dysfunction of a tissue 100 placed between the first electromagnetic coil 40 and the second electromagnetic coil 42 for treatment of an extracellular matrix disruption of a tissue placed between the electromagnetic coils.

The first electromagnetic coil 40 and second electromagnetic coil 42 can be oriented so that when they are energized using the pulse generator 10, a plurality of magnetic wave pulses can be generated with slew rates of at least 200 kG/s for at least a duration between about 0.1 microsecond to about 200 microseconds.

Also shown are the first electromagnetic coil second side 53 and the second electromagnetic coil first side 55.

Figure 6:
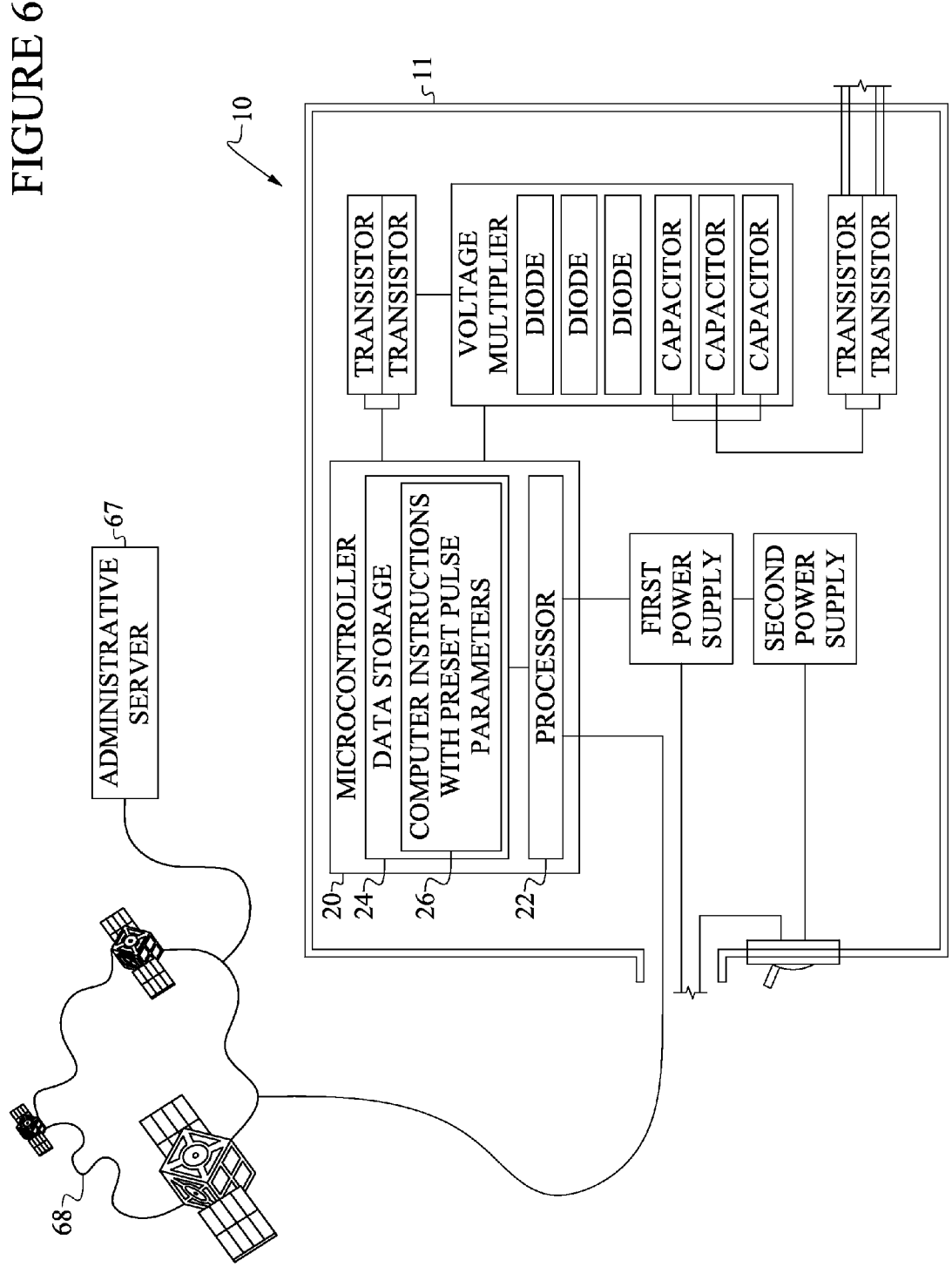
FIG. 6 is a diagram showing a processor in communication with an administrative server.

FIG. 6 shows an embodiment of the pulse generator 10 with the microcontroller 20 having a processor 22 in communication with at least one network 68 with an administrative server 67, that allows for online reconfiguration of the pulse generator.

Also shown are the housing 11, the data storage 24, and the computer instructions with preset pulse parameters 26.

Figure 7:
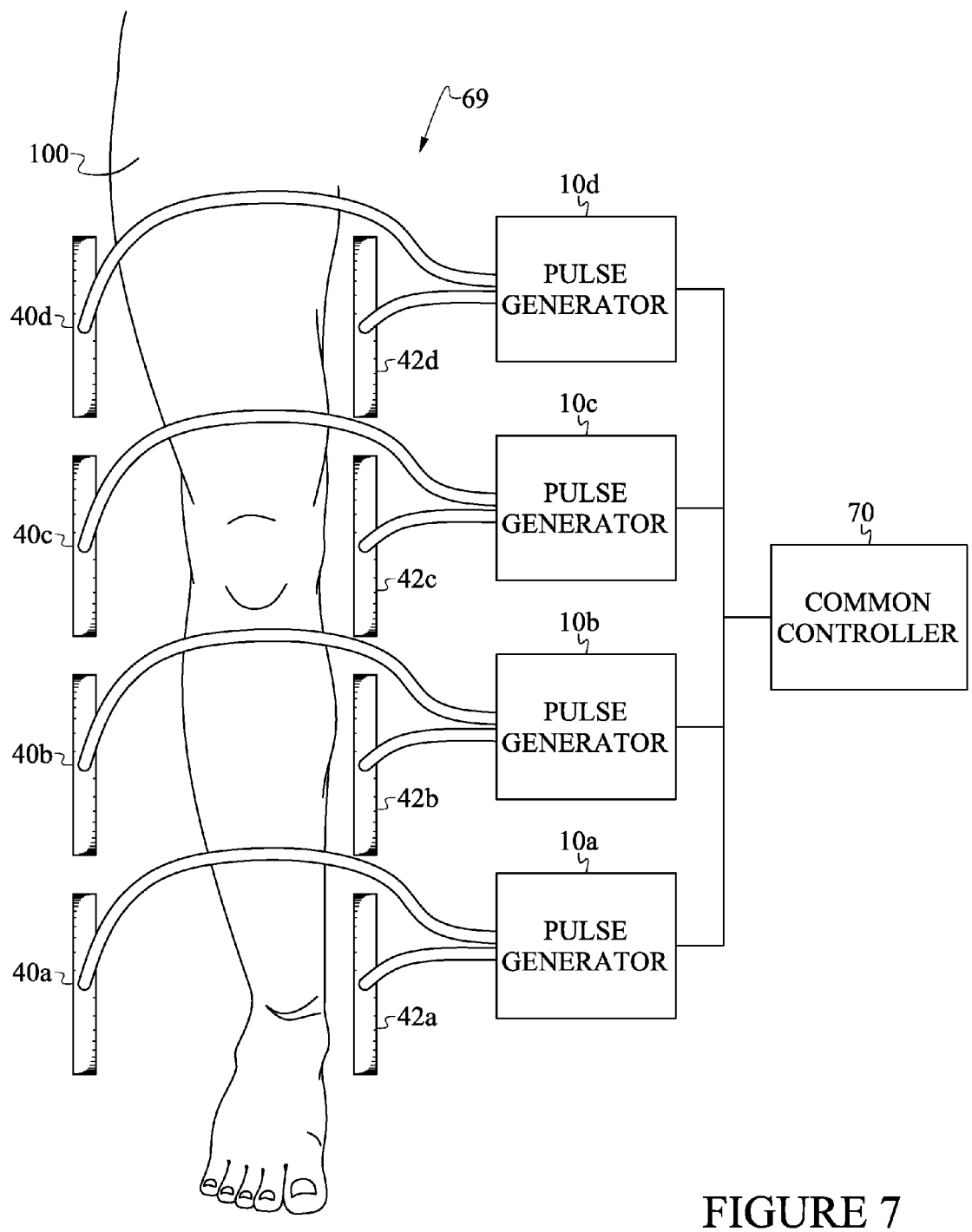
FIG. 7 is diagram of a magnetic array applied over a limb.

FIG. 7 shows four very low power electromagnetic coil pairs having first electromagnetic coils 40a, 40b, 40c, and 40d paired with second electromagnetic coils 42a, 42b, 42c, and 42d.

Each very low power electromagnetic coil pair is associated with a pulse generator 10a, 10b, 10c, and 10d. The pulse generators are controlled by a common controller 70.

The multiple pairs of very low power electromagnetic coils with pulse generators form an electromagnetic array 69 for treating a large area of tissue 100 that is capable of covering an entire limb, which is a leg in this view.

FIG. 8A shows an embodiment of a kit for therapeutically treating tissue ailments including cellular dysfunction of a tissue or an extracellular matrix disruption of a tissue, with an animal saddlebag 78, a first pouch 79, a pulse generator 10 in the first pouch 79, and a support strap 81.

FIG. 8B shows the opposite side of the animal shown in FIG. 8A. The animal saddlebag 78 is shown with a second pouch 80.

Within the second pouch 80 is a first electromagnetic coil 40, a second electromagnetic coil 42 and power supply 16.

The support strap 81 holds the first pouch 79 and the second pouch 80 together across the chest of the animal.

Figure 9:
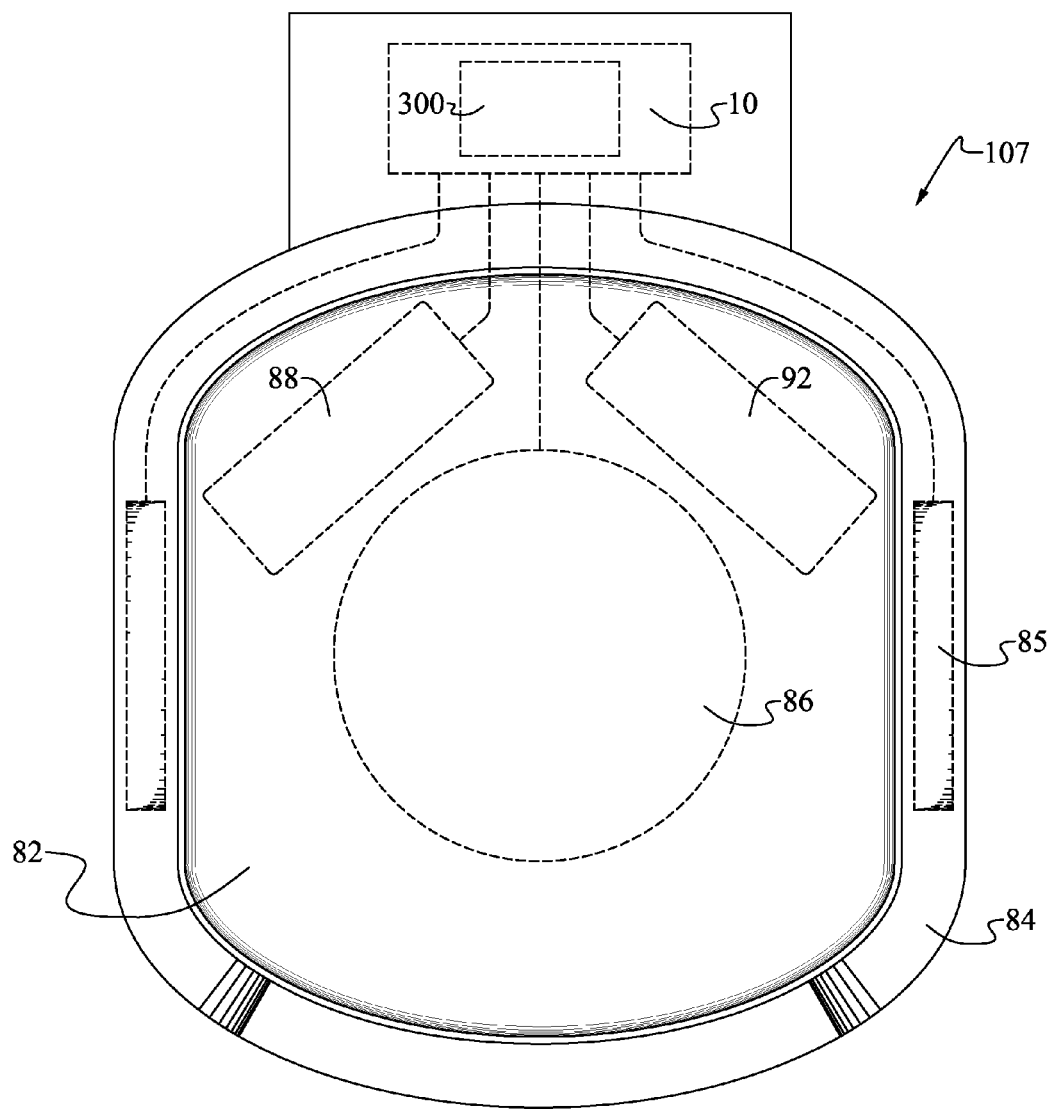
FIG. 9 is a view of a pet bed.

FIG. 9 shows and embodiment of a pet bed 107. The pet bed has bedding 82, a fabric housing 84 for containing the bedding 82, a Halbach array 85 disposed in the fabric housing 84, and an animal actuated on/off switch 86 connected to the Halbach array 85.

Also shown are a heating element 88 and a cooling element 92, each connected to a power supply 300 of the pulse generator 10.

Figure 10:
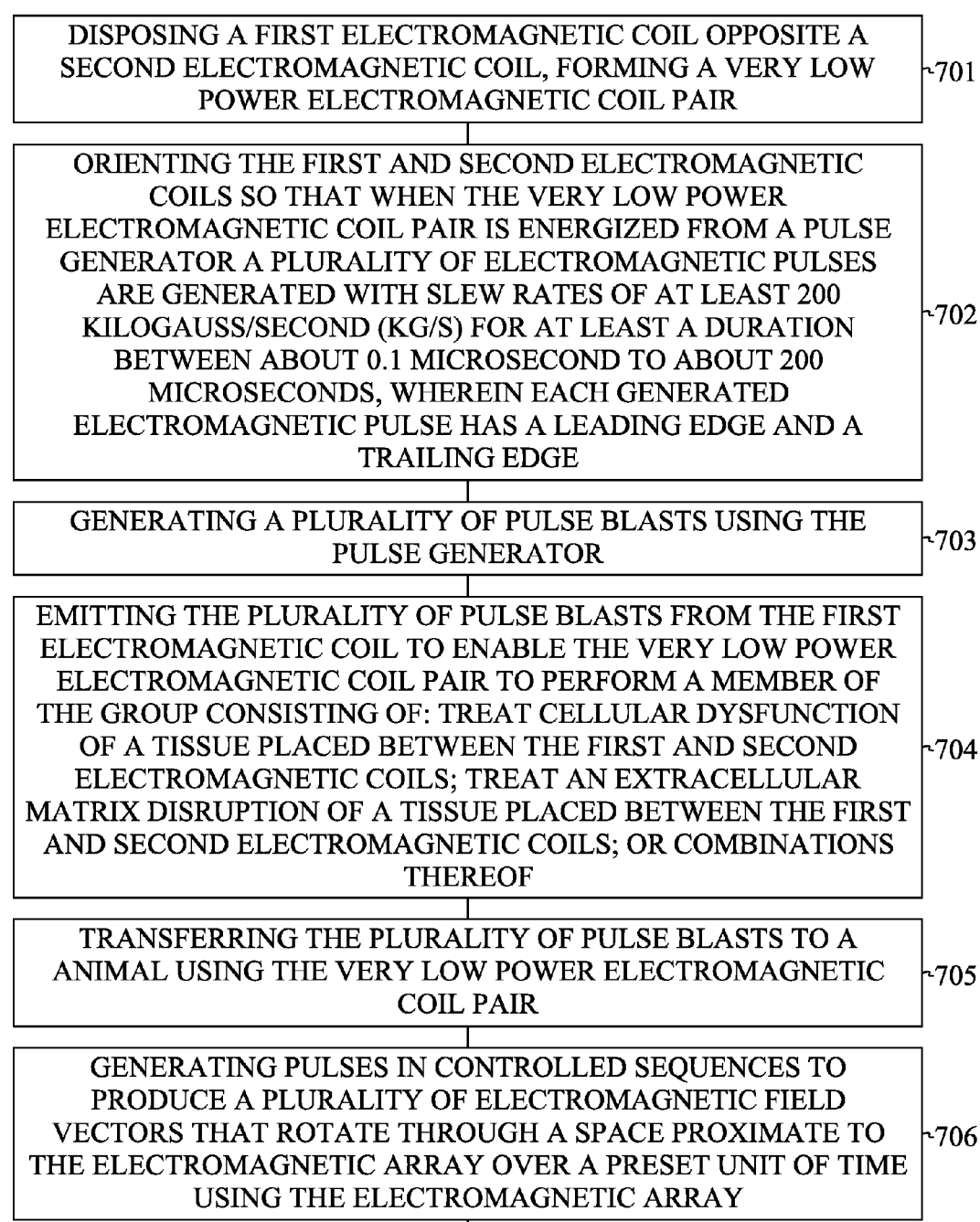
FIG. 10A is a flow diagram of an embodiment of the method.
FIG. 10B is a continuation of the flow diagram shown in FIG. 10A.

FIG. 10A shows an embodiment of a method for treating an animal.

A first step 701 can include disposing a first electromagnetic coil opposite a second electromagnetic coil, forming very low power electromagnetic coil pair.

A second step 702 can include orienting the first electromagnetic coil and the second electromagnetic coil so that when the very low power electromagnetic coil pair is energized from a pulse generator a plurality of electromagnetic pulses are generated with slew rates of at least 200 kiloGauss/second (kG/s) for at least a duration between about 0.1 microsecond to about 200 microseconds, wherein each generated electromagnetic pulse has a leading edge and a trailing edge.

A third step 703 can include generating a plurality of pulse blasts using the pulse generator.

A fourth step 704 can include emitting the plurality of pulse blasts from the first electromagnetic coil to enable the very low power electromagnetic coil pair to perform a member of the group consisting of: treat cellular dysfunction of a tissue placed between the first and second electromagnetic coils; treat an extracellular matrix disruption of a tissue placed between the first and second electromagnetic coils; or combinations thereof.

A fifth step 705 can include transferring the plurality of pulse blasts to an animal using the very low power electromagnetic coil pair.

A sixth step 706 can include generating pulses in controlled sequences to produce a plurality of electromagnetic field vectors that rotate through a space proximate to the electromagnetic array over a preset unit of time using the electromagnetic array.

FIG. 10B shows a continuation of the embodiment of a method for treating an animal shown in FIG. 10A.

A seventh step 707 can include generating pulse blasts in controlled sequences to produce a plurality of electromagnetic field vectors that translate through space proximate the electromagnetic array over time.

An eighth 708 can include generating pulse blasts at random intervals within specified ranges of pulse parameters using computer instructions in the data storage to instruct the processor.

A ninth step 709 can include producing unipolar electromagnetic pulses with leading edge electromagnetic slew rates greater than 200 kG/s and trailing edge magnetic slew rates less than 200 kG/s and using pulses with a duration longer than 200 microseconds.

A tenth step 710 can include adjusting pulse parameters to stimulate extracellular signals, trans-membrane signals, intracellular signals, or combinations thereof.

An eleventh step 711 can include adjusting pulse parameters to simulate a combination of signals associated with at least one member of the group consisting of: extracellular signals associated with mechanical loading of the target tissue; trans-membrane signals associated with mechanical loading of the target tissues; and intracellular signals associated with mechanical loading of the target tissues.

A twelfth step 712 can include employing pulses with randomized pulse parameters to prevent physiological accommodation or neural accommodation for treatment of chronic pain, acute pain, or combinations thereof.

FIG. 11 shows a diagram of an embodiment of a method for therapeutically treating an animal.

A first step 801 can include placing an animal saddlebag with a first pouch and a second pouch on an animal.

A second step 802 can include placing a pulse generator in the first pouch for generating a plurality of pulse blasts.

A third step 803 can include using a support strap to hold the first pouch and second pouch together across a chest of the animal.

A fourth step 804 can include placing a pair of very low power electromagnetic coils in communication with the pulse generator and a power supply within the second pouch.

A fifth step 805 can include capturing tissue of the animal between the pair of very low power electromagnetic coils or placing the pair of very low power electromagnetic coils adjacent tissue of the animal.

A sixth step 806 can include generating a plurality of pulse blasts using the pulse generator.

A seventh step 807 can include transferring the plurality of pulse blasts to the animal using the pair of very low power electromagnetic coils.

FIG. 12 shows a flow diagram for an embodiment of a method for therapeutically treating an animal using a pet bed.

A first step 901 can include containing a bedding within a fabric housing.

A second step 902 can include disposing a Halbach array in the fabric housing.

A third step 903 can include allowing an animal to actuate an on/off switch connected to the Halbach array, thereby generating magnetic pulse blasts using the Halbach array.

A fourth step 904 can include transferring the magnetic pulse blasts to the animal.

Figure 13:
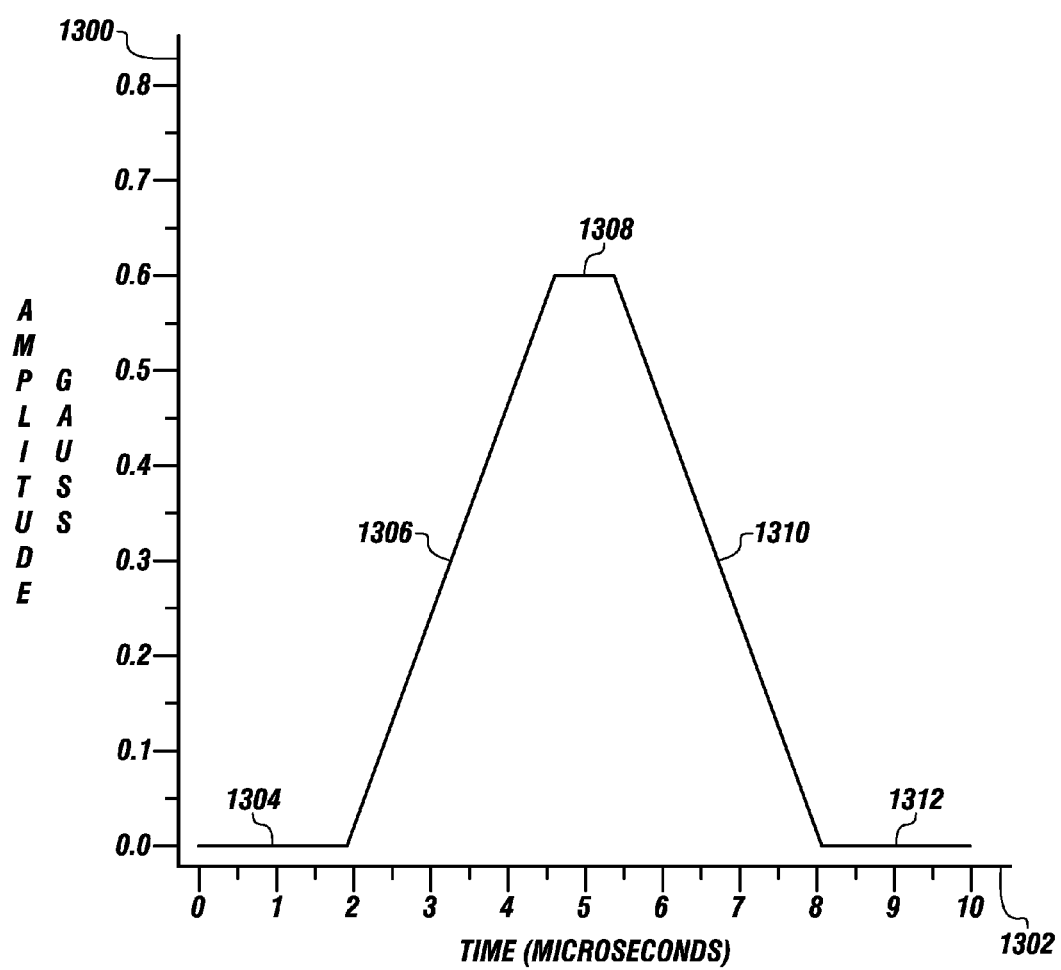
FIG. 13 is a representation of an idealized trapezoidal electromagnetic unipolar pulse that is generated by a microcontroller for use by the electromagnetic coil pair.

FIG. 13 is a representation of an idealized trapezoidal electromagnetic unipolar pulse. The curve has been idealized straight lines that may be curved.

In this Figure, a leading and trailing edge are shown where the slew rate can be determined graphically. Trapezoidal pulses need not be symmetric. Leading and trailing edges may have different slopes.

Element 1300 shows the y-axis. The units of this y-axis represent the amplitude of the magnetic field in Gauss.

Time is shown as element 1302, which is the x-axis and represents microseconds.

The element 1304 indicates a zero amplitude magnetic field, which is the beginning of this trapezoidal curve existing before a single electromagnetic pulse initiates from the pulse generator.

The leading edge of the electromagnetic pulse is shown as element 1306 with a slew rate of about 230 kiloGauss per second.

Element 1308 is the peak amplitude, which in this example is 0.6 Gauss.

The trailing edge of the electromagnetic pulse is shown as element 1310, which is shown here with the same slew rate as the leading edge.

Element 1312 is the zero amplitude magnetic field to which the signal returns at the completion of the pulse.

While these embodiments have been described with emphasis on the embodiments, it should be understood that within the scope of the appended claims, the embodiments might be practiced other than as specifically described herein.

What is claimed is:

1. A method for treating an animal having a tissue injury, tissue degeneration, an idiopathic pain, a cellular dysfunction of a tissue, or a dysfunction of an extracellular matrix of a tissue, wherein the method comprises:
   a. disposing a first electromagnetic coil proximate to a second electromagnetic coil, forming a very low power electromagnetic coil pair;
   b. placing a tissue proximate to the very low power electromagnetic coil pair;
   c. orienting the first electromagnetic coil and the second electromagnetic coil so that when the very low power electromagnetic coil pair is energized from a pulse generator, the very low power electromagnetic coil pair receives a plurality of shaped electromagnetic pulses, and wherein each shaped electromagnetic pulse is shaped over time to approximate a member of the group: a trapezoid, a polygon, a triangle, a Gaussian function; a Dirac delta function, or combinations thereof; and wherein the shaped electromagnetic pulses are generating having leading edges, trailing edges, or both, wherein each edge slew rate is at least 200 kiloGauss/second (kG/s) for at least a duration from 0.1 microsecond to 1000 microseconds without forming a sine shaped pulse wave; and
   d. generating at least one pulse blast, each pulse blast having at least one pulse, from the very low power electromagnetic coil pair, enabling the very low power electromagnetic coil pair to affect animal tissue and perform a member of the group consisting of:
      i. treat cellular dysfunction of the tissue placed proximate to the first electromagnetic coil and the second electromagnetic coil;
      ii. treat extracellular matrix disruption of the tissue placed proximate to the first electromagnetic coil and the second electromagnetic coil;
      iii. treat a tissue injury afflicting tissue proximate to the first electromagnetic coil and the second electromagnetic coil;
      iv. treat a tissue degeneration afflicting tissue proximate to the first electromagnetic coil and the second electromagnetic coil; and
      v. treat pain which is a member of the group consisting of:
         (a) acute or chronic pain arising from tissue degeneration;
         (b) acute or chronic pain arising from tissue injury;
         (c) acute or chronic pain arising from extracellular matrix disruption of tissue;
         (d) acute or chronic pain arising from cellular dysfunction of tissue;
         (e) acute or chronic pain of idiopathic origin associated with the tissue; and
            wherein the acute or chronic pain is treated by placing the tissue proximate to the first electromagnetic coil and the second electromagnetic coil; or combinations thereof.

2. The method of claim 1, further comprising using bipolar pulses as at least one of the pulses.

3. The method of claim 1, wherein the pulses are generated by a pulse generator comprising:
   a. a power supply;
   b. a bi-directional communication and power port for flowing power from the power supply into and out of the pulse generator and flowing communication signals into and out of the pulse generator;
   c. a microcontroller in communication with the bi-directional communication and power port, wherein the microcontroller further comprises a processor in communication with the power supply;
   d. a data storage in communication with the processor;
   e. computer instructions with preset pulse parameters in the data storage;
   f. a pair of first transistors in communication with the microcontroller;
   g. a voltage multiplier in communication with the pair of first transistors, wherein the voltage multiplier comprises a plurality of diodes and a plurality of capacitors in communication with the microcontroller for increasing or decreasing a voltage of the pulse generator;
   h. a pair of second transistors in communication with the plurality of capacitors, wherein the pair of second transistors produces an electrical signal that is transmitted to the very low power electromagnetic coil pair; and
   i. a pair of power supply conduits in communication with the pair of second transistors for transferring the electrical signal to the very low power electromagnetic pair.

4. The method of claim 3, wherein the pulse parameters controlled by the microcontroller are selected from the group consisting of: a pulse voltage or current, a pulse duration, a pulse polarity, a number of pulses per unit of time, a number of pulses per pulse blast, a time duration between pulses in each pulse blast, and at least one time duration between pulse blasts.

5. The method of claim 3, further comprising connecting an external power supply to the power supply to allow for uninterrupted pulse blast generation.

6. The method of claim 5, further comprising actuating the external power supply using an on/off switch.

7. The method of claim 3, further comprising connecting the plurality of capacitors and the pair of second transistors together in an H-bridge configuration.

8. The method of claim 3, further comprising using the microcontroller to perform on-line configuration or reconfiguration using communication from an administrative server.

9. The method of claim 8, further comprising providing wireless communication through at least one network between the administrative server and the microcontroller.

10. The method of claim 3, further comprising generating pulse blasts at random intervals within specified ranges of pulse parameters using computer instructions in the data storage to instruct the processor.

11. The method of claim 1, further comprising using positive polarity blasts, negative polarity blasts, or combinations thereof in the pulse blasts.

12. The method of claim 1, wherein the plurality of pulse blasts are a series of single pulses.

13. The method of claim 1, further comprising providing a dosage amount of pulse blasts to tissue by using a spacing between the first electromagnetic coil and the second electromagnetic coil that ranges from 0.1 to 20 times a radius of the electromagnetic coils.

14. The method of claim 1, wherein each electromagnetic coil has an axis about which the electromagnetic coil is concentric and further comprising aligning together both axes of the electromagnetic coils, wherein the axes are aligned either in a parallel arrangement, a coaxial arrangement, or a coplanar orientation.

15. The method of claim 1, further comprising using different quantities of pulses for different pulse blasts.

16. The method of claim 1, further comprising using varying intervals of time between each of the plurality of pulse blasts.

17. The method of claim 1, further comprising using the microcontroller to automatically sequence between predetermined sequences of pulses for predetermined intervals of time.

18. The method of claim 1, further comprising forming a plurality of pairs of electromagnetic coils into a connected electromagnetic array having a common controller for treating a large area of tissue.

19. The method of claim 18, further comprising generating individual pulses in controlled sequences to produce a plurality of magnetic field vectors that rotate through a space proximate to the electromagnetic array over a preset unit of time using the electromagnetic array.

20. The method of claim 18, further comprising generating electromagnetic pulse blasts in controlled sequences to produce a plurality of magnetic field vectors that translate through space proximate the electromagnetic array over time.

21. The method of claim 1, further comprising arranging a plurality of electromagnetic coils into a member of the group consisting of: a two-dimensional Halbach array, a one-dimensional Halbach array, or combinations thereof.

22. The method of claim 21, further comprising using at least one pair of electromagnetic coils of the Halbach array with an in-plane axis as flux conduit between a normal-to-plane axis of at least one adjacent pair of electromagnetic coils.

23. The method of claim 22, further comprising using a flux concentrator of iron, a flux concentrator of ferrite, or a flux concentrator of another magnetic material in each Halbach array to concentrate each magnetic field proximate to tissue within each Halbach array.

24. The method of claim 21, further comprising using a center-to-center distance between the normal-to-plane axis in each Halbach array ranging from 0.5 inches to 10 inches.

25. The method of claim 21, further comprising sealing each Halbach array within a mechanically flexible polymer coating which allows unimpeded generation of magnetic fields.

26. The method of claim 1, further comprising producing unipolar electromagnetic pulses with leading edge magnetic slew rates greater than 200 kG/s and trailing edge magnetic slew rates less than 200 kG/s and a duration longer than 200 microseconds.

27. The method of claim 1, wherein pulse parameters are adjusted to stimulate extracellular signals of the tissue, transmembrane signals of the tissue, intracellular signals of the tissue, or combinations thereof.

28. The method of claim 1, wherein pulse parameters of at least one pulse blast are adjusted to simulate a combination of signals associated with at least one member of the group consisting of:
   a. extracellular signals associated with mechanical loading of the tissue;

b. trans-membrane signals associated with mechanical loading of the tissue;

c. intracellular signals associated with mechanical loading of the tissue;

d. signals associated with nerve synapse signals to the tissue; or combinations thereof.

29. The method of claim 1, further comprising employing pulses with randomized pulse parameters to prevent physiologic accommodation or neural accommodation in the animal for treatment of chronic pain, acute pain, or combinations thereof.

* * * * *